US008205486B2

(12) United States Patent
Sri Ranjan

(10) Patent No.: US 8,205,486 B2
(45) Date of Patent: Jun. 26, 2012

(54) PLANT-CONTROLLED ATMOMETER FOR MEASURING CROP EVAPOTRANSPIRATION

(76) Inventor: Ramanathan Sri Ranjan, Winnipeg (CA)

( * ) Notice: Subject to any disclaimer, the term of this patent is extended or adjusted under 35 U.S.C. 154(b) by 370 days.

(21) Appl. No.: 12/709,592

(22) Filed: Feb. 22, 2010

(65) Prior Publication Data

US 2010/0212409 A1    Aug. 26, 2010

Related U.S. Application Data

(60) Provisional application No. 61/155,213, filed on Feb. 25, 2009.

(51) Int. Cl.
*G01N 25/56* (2006.01)
(52) U.S. Cl. .......................... 73/73; 73/61.77
(58) Field of Classification Search ............... 73/61.77, 73/73
See application file for complete search history.

(56) References Cited

U.S. PATENT DOCUMENTS

| 4,418,576 | A | * | 12/1983 | White | 73/61.77 |
| 5,311,769 | A | * | 5/1994 | Hetzel | 73/61.77 |
| 5,423,206 | A | * | 6/1995 | Hetzel | 73/61.77 |
| 6,048,091 | A | * | 4/2000 | McIntyre et al. | 374/54 |

* cited by examiner

*Primary Examiner* — Hezron E Williams
*Assistant Examiner* — Rodney T Frank
(74) *Attorney, Agent, or Firm* — Ryan W. Dupuis; Kyle R. Satterthwaite; Ade & Company Inc.

(57) ABSTRACT

An atmometer device comprises a porous evaporator member, a suction tube communicating water from a reservoir to the porous evaporator member, a sensor measuring a moisture characteristic of soil associated with a crop, a mechanism arranged for controllably varying a rate of evaporation of the water through the porous evaporator member responsive to the moisture characteristic measured by the sensor, and an indicator arranged to indicate water loss in the reservoir. By controlling rate of evaporation of the water through the porous evaporator member responsive to the measured moisture characteristic of the soil, the amount of water loss in the reservoir during the given time period more accurately reflects crop evapotranspiration.

20 Claims, 3 Drawing Sheets

Data on declining ET in response to lower soil moisture status

PLANT-CONTROLLED ATMOMETER FOR MEASURING CROP EVAPOTRANSPIRATION

This application claims the benefit under 35 U.S.C. 119(e) of U.S. provisional application Ser. No. 61/155,213, filed Feb. 25, 2009.

FIELD OF THE INVENTION

The present invention relates to an improved atmometer which is particularly suited for measuring crop evapotranspiration, and more particularly relates to an atmometer which is responsive to soil moisture conditions.

BACKGROUND

Accurate evapotranspiration (ET) data is essential for determining the depth of water to be applied through irrigation systems. At present, data from weather stations are used in empirical equations to predict evapotranspiration which is not site/crop specific and is prone to large errors. Alternatively, pan evaporation measurements and evaporation from porous plates (atmometers) have been used to measure the depth of evaporation and relate this measurement to ET using crop coefficients. However, plant evapotranspiration is controlled not only by weather conditions but also by soil water content. The atmometer, pan evaporation, and the weather-data based methods of predicting ET are not affected by soil water content and therefore do not take into account the plant response to soil moisture deficit as shown in the constant rate in FIG. 1. This error might lead to an over application of irrigation water.

Atmometers and pan evaporation meters have been used for over 50 years as a method to measure evaporation rate as affected by weather conditions. As noted above, this evaporation rate is multiplied by a crop coefficient to estimate evapotranspiration from a crop. When the soil is wet, the crops evapotranspire at the maximum rate just like the evaporation from an atmometer or a pan evaporation meter characterized by the weather limiting phase as shown in FIG. 1. However, when the soil becomes dry, the plants find it difficult to draw water from the soil leading to a decrease in evapotranspiration due to increased stomatal resistance.

Consequently, the plants tend to lower their ET rate by stomatal closure (wilting) at a rate to match decreased flow of water towards the roots through the dry soil within the root zone. This phenomenon is shown in FIG. 1 as a declining part of the graph located within the soil-limiting phase. However, the traditional atmometer or the pan evaporation meter is unresponsive to soil water content. Therefore, any estimation of ET based on evaporation from conventional atmometers will lead to an over-estimation of the ET. This will lead to over-application of irrigation water for crops, gardens, or golf courses.

SUMMARY OF THE INVENTION

According to one aspect of the invention there is provided a method of estimating crop evapotranspiration during a given time period, the method comprising:

providing an atmometer comprising a porous evaporator member, a reservoir for supplying water, maintained at constant head, to the porous evaporator member, and a suction tube for communicating water from the reservoir to the porous evaporator member;

measuring a moisture characteristic of the soil;

controllably varying a rate of evaporation of the water through the porous evaporator member responsive to the measured moisture characteristic of the soil; and determining an amount of water loss in the reservoir during the given time period.

The method may include varying the rate of evaporation by varying a resistance of the flow of water along the suction tube from the reservoir to the porous evaporator member. In a preferred embodiment, varying a resistance to the flow of water through the suction tube may be accomplished by varying an amount of porous medium the water must flow through.

Alternatively, the method may include varying the rate of evaporation of the water through the porous evaporator member by varying characteristics of the porous evaporator member.

The measured moisture characteristic of the soil may comprise a moisture content of the soil, a degree of soil suction or a measured soil resistance related to moisture content in the soil.

The moisture characteristic may be measured by burying a moisture sensor in a plant root zone of a crop.

In some embodiments, there may be provided a plurality of atmometers in a crop, each associated with a respective region of the crop such that crop evapotranspiration may be estimated according to region.

In a preferred embodiment, the amount of water loss of the reservoir may be determined by comparing weight of the reservoir before and after the given the time period.

According to another aspect of the present invention there is provided an atmometer device comprising:

a porous evaporator member;

a reservoir arranged for supplying water to the porous evaporator member;

a suction tube arranged for communicating water from the reservoir to the porous evaporator member;

a sensor arranged for measuring a moisture characteristic of soil associated with a crop;

a mechanism arranged for controllably varying a rate of evaporation of the water through the porous evaporator member responsive to the moisture characteristic measured by the sensor; and an indicator arranged to indicate water loss in the reservoir.

In the preferred embodiment, the mechanism is arranged to vary a resistance to water flow communicating through the suction tube from the reservoir to the porous evaporator member by varying an amount of porous medium that the water must flow through from the reservoir to the porous evaporator member. In this instance, the mechanism may further comprise a plurality of valves associated with respective passages through the porous medium, so that a controller may operate the valves to controllably vary the rate of evaporation of the water through the porous member.

When there is provided a water level sensor in the reservoir arranged to determine water loss in the reservoir, a transmitter may be arranged to transmit the determined water loss from the reservoir to a remote recording station. Preferably the recording station is arranged to communicate with a plurality atmometer devices of like configuration associated with different regions of the crop.

The plant-controlled atmometer device described herein overcomes the disconnect of the prior art by linking the atmometer response to soil water deficit. In this invention, the rate of evaporation from the porous plate of the atmometer is controlled by a mechanism connected to a sensor buried within the plant rootzone. If the soil is wet, the plants will evapotranspire at the maximum rate similar to the evaporation rate though the atmometer or a pan evaporation meter. However, as the soil becomes dry the plants will evapotranspire at a lower rate. Similarly, the sensor buried within the rootzone will activate the mechanism to decrease the evaporation rate through the atmometer. Thus the evaporation measured by the plant-controlled atmometer will closely mimic the ET of the plant. The change in volume of water within the plant-controlled atmometer can be directly read by the irrigator or the data can be transmitted via telemetry to a remote location where the irrigation system control is housed. Compared to existing methods, the plant-controlled atmometers are relatively inexpensive and multiple units can be used in a field to more accurately measure ET.

In a preferred embodiment, the soil water sensor buried within the rootzone of the crop will monitor the capillary pressure/soil water content. This data is transmitted to a mechanism within the atmometer that will directly control the evaporation rate through the porous membrane. As noted above, if the soil is dry, it will increase the resistance to evaporation from the atmometer. The larger the soil water deficit, the lower the evaporation rate from the atmometer. Therefore, the plant-controlled atmometer closely mimics the evapotranspiration of the plants by linking the rate of evaporation from the plant-controlled atmometer to capillary pressure/soil water content within the root zone of the crop. The plant-controlled atmometer can conserve valuable water by accurately predicting the depth of irrigation.

Some embodiments of the invention will now be described in conjunction with the accompanying drawings in which:

DETAILED DESCRIPTION

Figure 1:
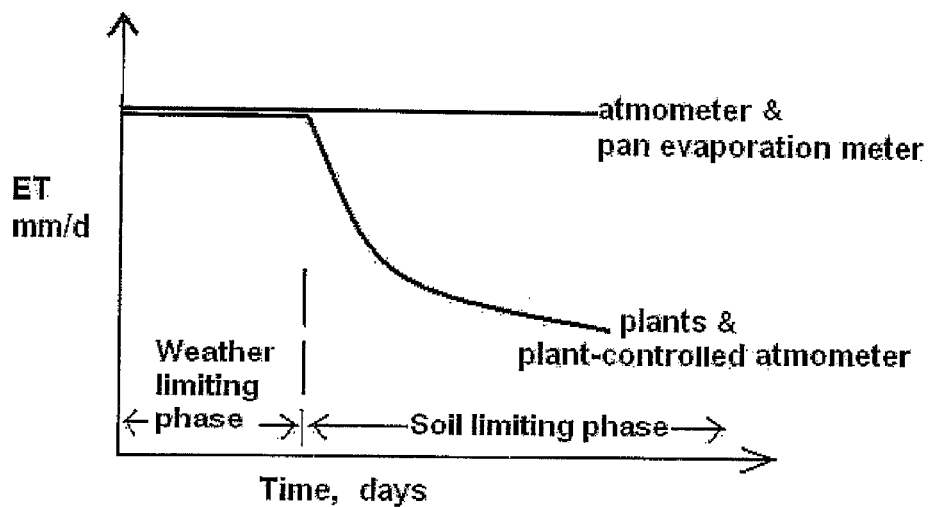
FIG. 1 is a graph illustrating evapotranspiration from plants and a plant controlled atmometer compared to a conventional atmometer and pan evaporation meter measurements as a function of time.
Figure 2:
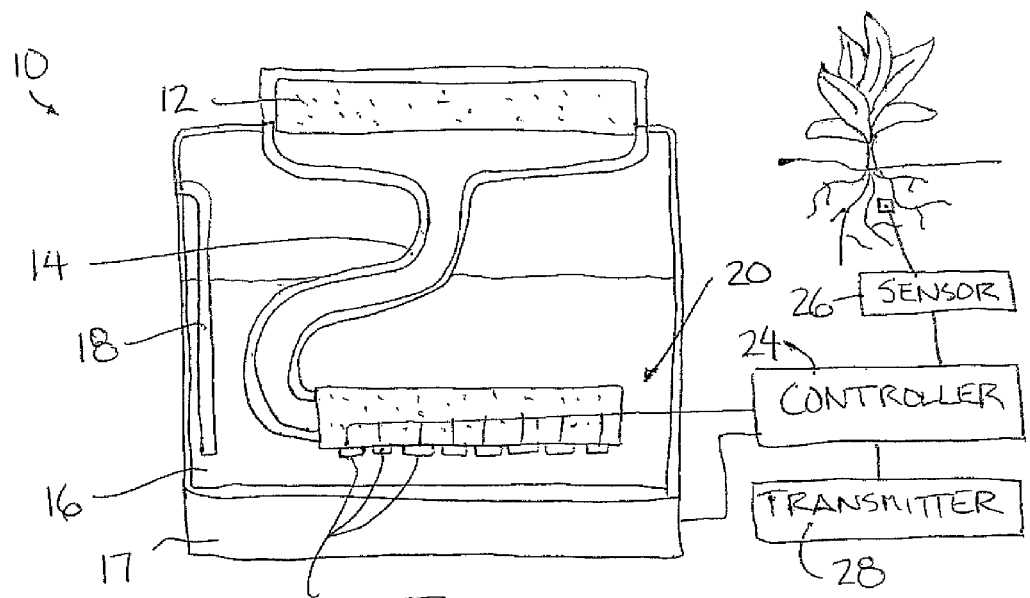
FIG. 2 is a schematic representation of a preferred embodiment of the atmometer device according to the present invention.

The general purpose of this invention is to accurately measure the crop evapotranspiration so that the depth of next irrigation can be determined. At present, there are no accurate methods available that are simple enough for ordinary farmers to use. The existing prior art atmometer is not responsive to soil moisture conditions and therefore does not reflect what is truly happening in the field.

Referring to the accompanying figures there is illustrated an atmometer device generally indicated by reference numeral 10. The device 10 is particularly suited for estimating crop evapotranspiration in a manner which is responsive to soil moisture conditions.

The device comprises an evaporator member formed of a porous plate which is wetted and arranged to permit evaporation from an upper surface thereof. The upper surface may include a suitable covering thereon to prevent rain seepage into the porous plate and to also simulate the evaporation from a crop canopy.

A suction tube 14 communicates with a bottom surface of the evaporator member 12 to supply the evaporator member with water from a suitable reservoir 16. The reservoir includes an indicator associated therewith for indicating to a user a content of water within the reservoir so that the user can determine an amount of water loss in the reservoir. When visually gauging the water loss in the reservoir, a tall narrow shape of reservoir is desirable for increased visual accuracy of the varying water levels in the reservoir. Alternatively, an inclined water level tube or sight gauge can be attached to the reservoir to increase the visual accuracy of the water level measurement by lengthening the sight gauge within a given height restriction of the reservoir. In the illustrated embodiment, the reservoir includes a suitable weight sensor 17 which is arranged to calculate a difference in weight indicative of a water loss in the reservoir and accordingly the reservoir can be of any shape without affecting the indication of water loss in the reservoir. The water loss is typically determined over a given period of time for example the period between irrigations of a crop which may be in the range of 10-14 days as an example.

The reservoir 16 is sealed with respect to the suction tube 14 communicating between the reservoir and the evaporator member except for an air passage 18 communicating through the wall of the reservoir between a top end above an uppermost water level in the reservoir externally of the reservoir and a bottom end at a fixed elevation terminating within the interior of the reservoir so as to remain submerged near a bottom end of the reservoir. The air passage ensures that suction of water in the suction tube on the bottom side of the evaporator member 12 remains constant despite varying water levels in the sealed reservoir, thereby, maintaining a constant head which is not affected by the water level within the reservoir.

The atmometer device 10 includes a suitable mechanism 20 which is arranged to vary the rate of evaporation of water through the porous evaporator in a controlled manner responsive to moisture conditions of the soil monitored by the atmometer device. In the illustrated embodiment, the mechanism 20 comprises a porous medium, for example clay or other suitable materials which allow a restricted flow of water therethrough. The porous medium communicates between a plurality of different inlets 22 in communication adjacent a bottom end of the reservoir and the suction tube in communication with the evaporator member 12. Each of the inlets 22 includes a respective valve associated therewith for defining a respective flow path through the porous medium from the fluid in the surrounding reservoir to the inlet of the suction tube in which each path has a varying resistance to the flow of water from the reservoir through the suction tube to the evaporator member 12.

A controller 24 is provided which operates the valves on the inlets 22 of the porous medium to vary the amount of porous medium that the water must flow through the suction tube to the evaporator member 12. By increasing the amount of porous medium the water must flow through, resistance to the flow through the suction tube is increased which in turn increases the amount of suction on the bottom face of the porous plate to effectively lower the rate of evaporation of water from the upper surface of the plate.

In further embodiments the rate of evaporation may be controllably varied by varying a height of the communication of the air passage 18 with the fluid in the reservoir. In yet a further arrangement, evaporation from the evaporator member 12 may be varied by varying a characteristic of the plate, for example an exposed surface area of the plate.

In either instance, the rate of evaporation is varied according to a moisture condition of the soil measured by a suitable sensor 26 which is arranged to be buried in the root zone of a crop being monitored. The sensor is arranged to measure a moisture characteristic of the soil for example a moisture content of the soil or soil suction in the form of capillary pressure in the soil. A preferred type of moisture sensor 26 is a commercially available moisture meter which uses a gypsum block supported in the soil. The sensor 26 may further be configured for measuring an electrical resistance of the soil which is related to the moisture content.

In either instance, the controller 24 of the present invention is arranged to increase the resistance to the flow of water through the suction tube when the sensor 26 determines that the soil is in a drier condition where evapotranspiration from the crop is reduced. Alternatively, when the sensor 26 determines wetter conditions of the soil resulting in an optimal increased evapotranspiration of the crop, resistance of the flow through the suction tube to the evaporator member 12 is reduced so that the evaporation from the evaporation member 12 most closely represents the actual evapotranspiration of the crop being monitored.

In some embodiments a plurality of atmometer devices of like configuration are located in various regions of a given crop for determining different water losses of the soil as a result of evapotranspiration in different regions of the crop. Alternatively, a plurality of root zone sensors may be provided within one region of a crop for collectively determining the moisture characteristics of the region to which a single atmometer device reacts. In either instance when providing a plurality of sensors or atmometer devices distributed about a crop, the water loss of the reservoir is preferably determined electronically by a suitable sensor 17 for communication by the controller 24 to a transmitter 28 which relays the water loss information to a common recording station remote from the sensors of the atmometers.

Figure 3:
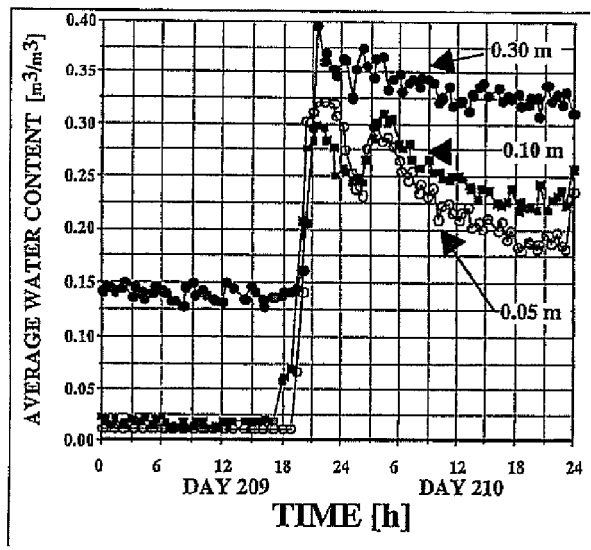
FIG. 3 is a graphical representation of soil water content measured at various soil depths subsequent to irrigation and rain.
Figure 4:
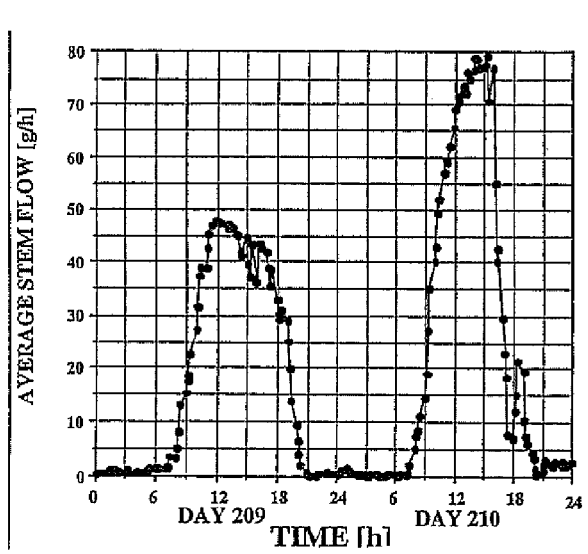
FIG. 4 is a graphical representation of stem flow rate from cotton before and after irrigation clearly showing the plant response to soil water deficit.
Figure 5:
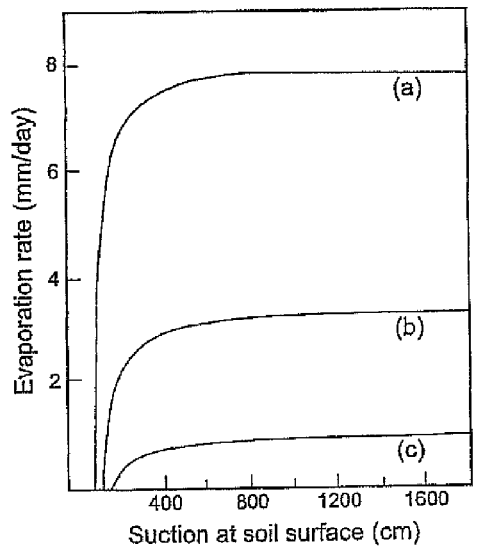
FIG. 5 is a graphical representation of evaporation from a water table as a function of the suction prevailing at the soil surface for various water table depths.
Figure 6:
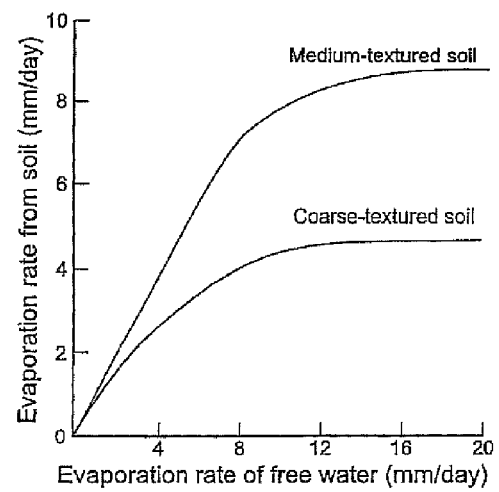
FIG. 6 is a graphical representation of a relationship between evaporation rate from different soil textures and evaporation rate from a free water surface.
Figure 7A:
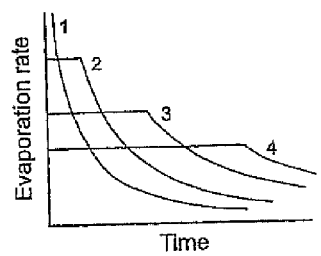
FIG. 7A is a graphical representation of evaporation rate versus time under different evaporativities.
Figure 7B:
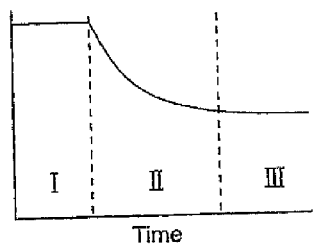
FIG. 7B is a graphical representation of the relation of relative evaporation rate versus time indicating three stages of the drying process.

FIG. 3 shows the soil water content at three different depths on two consecutive days before and after irrigation/rain in a Cotton crop. The ET represented by average stem flow has increased from 47 g/h to 79 g/h due to an increase in soil water content (volumetric basis) from 0.15 to 0.33 at a depth of 0.3 m below the ground surface. This is clear indication that the plant ET rate is highly responsive to soil water content towards the later days of the irrigation interval.

The conventional Atmometer and the Pan Evaporation Method do not account for this plant response to soil moisture status. Yet, millions of units are used around the world to schedule irrigation, resulting in over-estimation of the plant water use by over 70% i.e. 79 g/h instead of 47 g/h.

The proposed plant-controlled atmometer will closely mimic the plant water use, leading to a large reduction in irrigation water use that will otherwise be wasted as deep percolation.

As described herein, the present invention relates to the creation of the link between the evaporation rates from the atmometer to the soil water status within the root zone. None of the traditional methods have this link. The main advantage of this invention is it enables us to accurately measure ET by mimicking crop evapotranspiration.

Two variations of the atmometer device are contemplated. The first is a low-cost plant-controlled atmometer that can be directly read by the farmer on a daily, weekly, or per irrigation cycle basis to make irrigation decision. The second product will have the capability to transmit the ET data directly via telemetry to another location.

The existing atmometers are not accurate in predicting ET because the correlation is about 70% at best. That is 30% error in estimation of ET and 30% waste of water! There are no current solutions to the problem of disconnect between the conventional atmometer and soil water status. The plant-controlled atmometer will more accurately estimate of ET. The plant-controlled atmometer is inexpensive and simple for the farmer to use.

The plant-controlled atmometer has the potential to be used world-wide because of the scarcity of water for irrigation. A 30% savings in water will translate to 30% increase in irrigated agriculture. Many companies sell weather stations for predicting ET and our product will be in direct competition to the weather stations used in ET prediction for irrigation scheduling. Weather station based methods suffer from the same draw back i.e. soil water status is ignored. The low-cost non-recording version of the product is simple enough for use by farmers in developing countries.

Irrigation companies, Irrigators, Golf courses, farmers, and people with large lawns are some of the potential end-users. It can be used as research tools by hydrologists, and foresters studying water balance in a watershed.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of estimating crop evapotranspiration during a given time period, the method comprising:
    providing an atmometer comprising a porous evaporator member, a reservoir for supplying water to the porous evaporator member and being arranged to be maintained at constant head, and a suction tube for communicating water from the reservoir to the porous evaporator member;
    measuring a moisture characteristic of the soil;
    controllably varying a rate of evaporation of the water through the porous evaporator member responsive to the measured moisture characteristic of the soil; and
    determining an amount of water loss in the reservoir during the given time period.

2. The method according to claim 1 including varying the rate of evaporation by varying a resistance of the flow of water along the suction tube from the reservoir to the porous evaporator member.

3. The method according to claim 2 including varying a resistance to the flow of water through the suction tube by varying an amount of porous medium the water must flow through.

4. The method according to claim 1 including varying the rate of evaporation of the water through the porous evaporator member by varying characteristics of the porous evaporator member.

5. The method according to claim 1 including measuring a moisture characteristic comprising a moisture content of the soil.

6. The method according to claim 1 including measuring a moisture characteristic of the soil comprising soil suction.

7. The method according to claim 1 including measuring a moisture characteristic of the soil comprising a soil resistance.

8. The method according to claim 1 including measuring a moisture characteristic of the soil by burying a moisture sensor in a plant root zone of a crop.

9. The method according to claim 1 including providing a plurality of atmometers in a crop, each associated with a respective region of the crop and estimating crop evapotranspiration according to region.

10. The method according to claim 1 including determining the amount of water loss of the reservoir by comparing weight of the reservoir before and after the given time period.

11. The method according to claim 1 including providing a constant head air inlet tube arranged to eliminate an effect of the water level within the reservoir on the evaporation rate.

12. An atmometer device comprising:
a porous evaporator member;
a reservoir arranged for supplying water to the porous evaporator member and arranged to be maintained at constant head pressure;
a suction tube arranged for communicating water from the reservoir to the porous evaporator member;
a sensor arranged for measuring a moisture characteristic of soil associated with a crop;
a mechanism arranged for controllably varying a rate of evaporation of the water through the porous evaporator member responsive to the moisture characteristic measured by the sensor; and
an indicator arranged to indicate water loss in the reservoir.

13. The device according to claim 12 wherein the mechanism is arranged to vary a resistance to water flow communicating through the suction tube from the reservoir to the porous evaporator member.

14. The device according to claim 13 wherein the mechanism is arranged to vary an amount of porous medium that the water must flow through from the reservoir to the porous evaporator member.

15. The device according to claim 14 wherein the mechanism comprises a plurality of valves associated with respective passages through the porous medium and wherein there is provided a controller for operating the valves to controllably vary the rate of evaporation of the water through the porous member.

16. The device according to claim 12 wherein the sensor is arranged to be buried in a plant root zone.

17. The device according to claim 12 wherein there is provided a water level sensor in the reservoir arranged to determine water loss in the reservoir and a transmitter arranged to transmit the determined water loss from the reservoir to a remote recording station.

18. The device according to claim 17 wherein the recording station is arranged to communicate with a plurality atmometer devices of like configuration.

19. The device according to claim 12 wherein the indicator is arranged to determine water loss in the reservoir according the weight loss of the reservoir.

20. The device according to claim 12 wherein there is provided a constant-head air inlet tube arranged to eliminate an effect of the water level within the reservoir on the evaporation rate.

* * * * *